United States Patent
Dominguez et al.

(10) Patent No.: US 8,859,815 B2
(45) Date of Patent: Oct. 14, 2014

(54) SULPHONYLATED DIPHENYLETHYLENEDIAMINES, METHOD FOR THEIR PREPARATION AND USE IN TRANSFER HYDROGENATION CATALYSIS

(75) Inventors: Beatriz Dominguez, Suffolk (GB); Antonio Zanotti-Gerosa, Cambridge (GB); Gabriela Alexandra Grasa, Mantua, NJ (US); Jonathan Alan Medlock, Cambridge (GB)

(73) Assignee: Bial-Portela & C.A., S.A., S. Mamede do Coronado (PT)

( * ) Notice: Subject to any disclaimer, the term of this patent is extended or adjusted under 35 U.S.C. 154(b) by 3 days.

(21) Appl. No.: 13/313,889

(22) Filed: Dec. 7, 2011

(65) Prior Publication Data

US 2012/0077973 A1    Mar. 29, 2012

Related U.S. Application Data

(63) Continuation of application No. 12/493,043, filed on Jun. 26, 2009, now abandoned, which is a continuation of application No. 11/719,478, filed as application No. PCT/GB2005/050190 on Nov. 1, 2005, now Pat. No. 7,667,075.

(51) Int. Cl.
| | |
|---|---|
| *C07C 311/13* | (2006.01) |
| *C07C 311/14* | (2006.01) |
| *C07C 311/16* | (2006.01) |
| *C07C 33/20* | (2006.01) |
| *C07C 33/22* | (2006.01) |
| *C07C 33/46* | (2006.01) |
| *C07C 303/38* | (2006.01) |
| *B01J 31/18* | (2006.01) |
| *C07C 29/143* | (2006.01) |
| *C07C 311/18* | (2006.01) |

(52) U.S. Cl.
CPC ........ B01J 31/1805 (2013.01); *B01J 2531/847* (2013.01); C07C 29/143 (2013.01); *B01J 2231/643* (2013.01); *B01J 2531/845* (2013.01); *B01J 2531/827* (2013.01); *C07B 2200/07* (2013.01); *B01J 2531/842* (2013.01); *B01J 2531/821* (2013.01); C07C 311/18 (2013.01); *B01J 2531/828* (2013.01); *B01J 2531/822* (2013.01); *B01J 2531/824* (2013.01)
USPC ............ 564/99; 564/89; 564/90; 564/92; 568/808; 568/812; 568/814; 502/166; 502/167

(58) Field of Classification Search
USPC .............. 564/92; 568/630, 812, 814; 502/155
See application file for complete search history.

(56) References Cited

U.S. PATENT DOCUMENTS

| | | | |
|---|---|---|---|
| 6,300,509 | B1 | 10/2001 | Crameri et al. |
| 6,723,871 | B2 | 4/2004 | Tada et al. |
| 7,045,646 | B2 | 5/2006 | Tanis et al. |
| 7,169,938 | B2 | 1/2007 | Eckert et al. |
| 7,232,927 | B2 | 6/2007 | Bosch et al. |
| 7,250,526 | B2 | 7/2007 | Blacker et al. |
| 7,667,075 | B2 | 2/2010 | Dominguez et al. |
| 7,754,889 | B2 | 7/2010 | Amano et al. |
| 2009/0326274 | A1 | 12/2009 | Dominguez et al. |

FOREIGN PATENT DOCUMENTS

| | | |
|---|---|---|
| CN | 1566084 A | 1/2005 |
| EP | 0916637 A1 | 5/1999 |
| EP | 1258470 A2 | 11/2002 |
| EP | 1439159 A1 | 7/2004 |
| EP | 1512678 A1 | 3/2005 |
| EP | 1812384 A1 | 8/2007 |
| JP | 2003034665 A | 7/2003 |
| JP | 2006511559 A | 4/2006 |
| WO | 0076942 A1 | 12/2000 |
| WO | 2004031155 A1 | 4/2004 |
| WO | 2006054115 A1 | 5/2006 |

OTHER PUBLICATIONS

Corey, E. J., et al., "Convenient Routes to Symmetrical Benzils and Chiral 1,2-Diaryl-1,2-diaminoethanes, Useful Controllers and Probes for Enantioselective Synthesis," Tetrahedron: Asymmetry, 1995, pp. 3-6, vol. 6, No. 1, Elsevier Science Ltd, Great Britain.

(Continued)

*Primary Examiner* — Brian J Davis
(74) *Attorney, Agent, or Firm* — Conley Rose, P.C.; Rodney B. Carrol

(57) ABSTRACT

A diamine of formula (I) is described in which A is hydrogen or a saturated or unsaturated C1-C20 alkyl group or an aryl group; B is a substituted or unsubstituted C1-C20 alkyl, cycloalkyl, alkaryl, alkaryl or aryl group or an alkylamino group and at least one of $X^1, X^2, Y^1, Y^2$ or Z is a C1-C10 alkyl, cycloalkyl, alkaryl, aralkyl or alkoxy substituting group. The chiral diamine may be used to prepare catalysts suitable for use in transfer hydrogenation reactions.

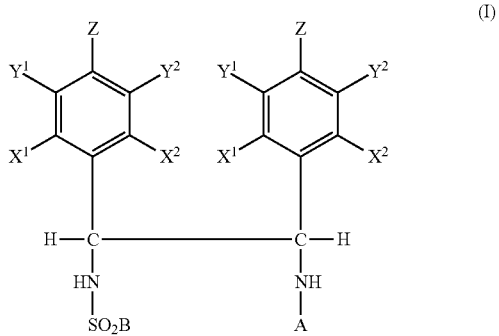

23 Claims, No Drawings

(56) References Cited

OTHER PUBLICATIONS

Foreign communication from a related counterpart application—International Preliminary Report on Patentability, PCT/GB2005/050190, May 22, 2007, 7 pages.

Foreign communication from a related counterpart application—International Search Report and Written Opinion, PCT/GB2005/050190, Feb. 17, 2006, 10 pages.

Foreign communication from a related counterpart application—Examination report, European Patent Application No. 05803157.6, Sep. 5, 2007, 2 pages.

Foreign communication from a related counterpart application—Examination report, European Patent Application No. 05803157.6, May 27, 2008, 4 pages.

Foreign communication from a related counterpart application—Result of consultation, European Patent Application No. 05803157.6, Jul. 22, 2009, 2 pages.

Foreign communication from a related counterpart application—Examination report, European Patent Application No. 05803157.6, Jul. 22, 2009, 3 pages.

Foreign communication from a related counterpart application—Result of consultation, European Patent Application No. 05803157.6, Feb. 15, 2010, 3 pages.

Foreign communication from a related counterpart application—Intention to grant, European Patent Application No. 05803157.6, Feb. 26, 2010, 21 pages.

Foreign communication from a related counterpart application—Communication, European Patent Application No. 05803157.6, Nov. 19, 2010, 2 pages.

Foreign communication from a related counterpart application—Examination report, European Patent Application No. 05803157.6, Nov. 23, 2010, 4 pages.

Foreign communication from a related counterpart application—Examination report, European Patent Application No. 05803157.6, May 30, 2011, 4 pages.

Foreign communication from a related counterpart application—Communication, European Patent Application No. 05803157.6, Mar. 7, 2012, 4 pages.

Ide, Walter S., et al., "The Synthesis of Benzoins", Chapter 5 of "Organic Reactions, vol. IV," 1948, pp. 269-304 plus cover, publishing, and content pages, editor-in-chief and copyright: Roger Adams, publisher: John Wiley & Sons, Inc., New York.

Li, Xiaoguang, et al., "Asymmetric transfer hydrogenation of ketones with a polymer-supported chiral diamine," Tetrahedron Letters, 2004, pp. 951-953, vol. 45, Elsevier Ltd.

Li, Xiaoguang, et al., "Asymmetric Transfer Hydrogenation in Water with a Supported Noyori-lkariya Catalyst," Organic Letters, 2004, pp. 3321-3324, vol. 6, No. 19, American Chemical Society.

Ma, Yaping, et al., "Asymmetric Transfer Hydrogenation of Prochiral Ketones in Aqueous Media with New Water-Soluble Chiral Vacinal Diamine as Ligand," Organic Letters, 2003, pp. 2103-2106, vol. 5, No. 12, American Chemical Society.

Mohar, Barbara, et al., "Highly enantioselective synthesis via dynamic kinetic resolution under transfer hyrogenation using Ru(•6-arene)-N-perfluorosulfonyl-1,2-diamine catalysts: a first insight into the relationship of the ligand's pKa and the catalyst activity," Chem. Commun., 2001, pp. 2572-2573, The Royal Society of Chemistry.

Noyori, Ryoji, et al., "Asymmetric Transfer Hydrogenation Catalyzed by Chiral Ruthenium Complexes," Accounts of Chemical Research, 1997, vol. 30, No. 2, pp. 97-102, American Chemical Society.

Office Action dated Feb. 4, 2010 (10 pages), U.S. Appl. No. 12/493,043, filed Jun. 26, 2009.

Office Action (Final) dated Jul. 7, 2011 (6 pages), U.S. Appl. No. 12/493,043, filed Jun. 26, 2009.

Pikul, S., et al., Chemical Abstract, 1995, 3 pages, 122:9562, ACS on STN.

Rhyoo, Hae Yoon, et al., "Use of surfactants in water-soluble ruthenium(II) complex-catalyzed asymmetric hydrogen-transfer reduction of aromatic ketones," Tetrahedron Letters, 2002, pp. 269-272, vol. 43, Elsevier Science Ltd.

Weiss, Marvin, et al., "The Catalytic Oxidation of Benzoin to Benzil," Journal of the American Chemical Society, 1948, p. 3666 plus one page publishing information, vol. 70, No. 11.

Xue, Dong, et al., "Transfer Hydrogenation of Activated C=C Bonds Catalyzed by Ruthenium Amido Complexes: Reaction Scope, Limitation, and Enantioselectivity," J. Org. Chem., 2005, pp. 3584-3591, vol. 70, No. 9, American Chemical Society.

Yamashita, Hiroshi, et al., "Practical Synthesis of Both Enantiomers of Vasopressin V2 Receptor Antagonist OPC-41061 Using the Catalytic Asymmetric Hydrogenation," 2002, pp. 123-128, vol. 56, Heterocycles.

Foreign communication from a related counterpart application—Examination report, Australian Application No. 2005305640, Apr. 30, 2010, 2 pages.

Foreign communication from a related counterpart application—Office action, Canadian Application No. 2,587,726, Apr. 20, 2012, 3 pages.

Foreign communication from a related counterpart application—First office action with translation, Chinese Application No. 200580046759.2, Oct. 16, 2009, 8 pages.

Foreign communication from a related counterpart application—Second office action with translation, Chinese Application No. 200580046759.2, Oct. 21, 2010, 4 pages.

Foreign communication from a related counterpart application—Third office action with translation, Chinese Application No. 200580046759.2, Aug. 18, 2011, 4 pages.

Foreign communication from a related counterpart application—Search report, European Application No. 08004008.2, May 28, 2008, 6 pages.

Foreign communication from a related counterpart application—Communication, European Application No. 08004008.2, Apr. 28, 2009, 1 page.

Foreign communication from a related counterpart application—Communication, European Application No. 08004008.2, Sep. 24, 2010, 4 pages.

Foreign communication from a related counterpart application—First examination report, Indian Application No. 3971/DELNP/2007, Oct. 29, 2012, 2 pages.

Foreign communication from a related counterpart application—Translation of office action, Japanese Application No. 2007-542126, Aug. 30, 2011, 2 pages.

Foreign communication from a related counterpart application—Office action with translation, Japanese Application No. 2007-542126, Nov. 6, 2012, 10 pages.

Foreign communication from a related counterpart application—Office action with translation, Korean Application No. 10-2007-7013467, Jul. 3, 2012, 9 pages.

Foreign communication from a related counterpart application—Examination report with translation, Russian Application No. 2007122501/04, 2009, 4 pages.

Foreign communication from a related counterpart application—Examination report with translation, Russian Application No. 2007122501/04, Feb. 1, 2010, 5 pages.

Foreign communication from a related counterpart application—Examination report with translation, Russian Application No. 2007122501/04, Feb. 25, 2011, 4 pages.

Foreign communication from a related counterpart application—Examination report with translation, Ukraine Application No. 200706770/, Dec. 10, 2008, 4 pages.

Foreign communication from a related counterpart application—Examination report with translation, Ukraine Application No. 200706770/, Oct. 2009, 3 pages.

SULPHONYLATED DIPHENYLETHYLENEDIAMINES, METHOD FOR THEIR PREPARATION AND USE IN TRANSFER HYDROGENATION CATALYSIS

CROSS-REFERENCE TO RELATED APPLICATIONS

This is a continuation application claiming priority to U.S. patent application Ser. No. 12/493,043 filed Jun. 26, 2009, published as U.S. Patent Publication 2009/0326274 A1, now abandoned, which is a continuation application claiming priority to U.S. patent application Ser. No. 11/719,478, filed Jul. 17, 2007, now U.S. Pat. No. 7,667,075, both entitled "Sulphonylated Diphenylethylenediamines, Method for their Preparation and Use in Transfer Hydrogenation Catalysis." The parent application, U.S. patent application Ser. No. 11/719,478, is a filing under 35 U.S.C. 371 of International Application No. PCT/GB2005/050190 filed Nov. 1, 2005, entitled "Sulphonylated Diphenylethylenediamines, Method for their Preparation and Use in Transfer Hydrogenation Catalysis," claiming priority of United Kingdom Patent Application No. 0425320.9 filed Nov. 17, 2004. The above identified patent and applications are incorporated by reference herein in their entirety.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

This invention relates to diamines and in particular to substituted diphenylethylenediamines and catalysts derived therefrom. Such catalysts are useful for accelerating asymmetric hydrogenation reactions whose products are useful, for example, as chemical intermediates or reagents for use in the production of fine chemicals or pharmaceutical intermediates.

Catalytic asymmetric hydrogenation involves the activation of molecular hydrogen with chiral metal complexes. However, organic molecules can also be applied as the hydrogen donor in the presence of a suitable chiral catalyst in a process known as transfer hydrogenation. A hydrogen donor such as isopropanol or formic acid is conventionally used with catalysts of the type [(sulphonylated diamine)RuCl (arene)] for the reduction of carbonyl groups. This technology provides a powerful complement to catalytic asymmetric hydrogenation. Transfer hydrogenation, in fact, is particularly suitable for the asymmetric reduction of ketones that are difficult substrates for hydrogenation, such as acetylenic ketones and cyclic ketones.

Heretofore the sulphonylated diamine component of the transfer hydrogenation catalysts has been limited to sulphonylated diphenylethylenediamine (Dpen) and cycloalkyl-1,2-diamines such as 1,2-cyclohexane. For example transfer hydrogenation has been applied using [(tosyl-dpen)RuCl (arene)] catalysts to pharmaceutical products such as 10-hydroxy-dihydro-dibenz-[b,f]-azepines (see WO 2004/031155).

The sulphonylated diamine components used heretofore, while useful, are not equally effective across the range of desirable substrates. Thus, there is a need to expand the range of diamines suitable for use in transfer hydrogenation catalysts that provide catalysts of increased activity, selectivity or stability. We have recognised that, by introducing one or more substituting groups into the phenyl rings of diphenylethylenediamines and by variation of the sulphonate properties, the steric and electronic properties of the diamine component may be usefully adapted.

SUMMARY

Accordingly the present invention provides a diamine of formula (I)

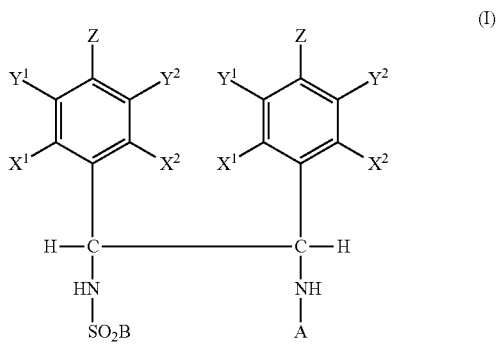

(I)

in which A is hydrogen or a saturated or unsaturated C1-C20 alkyl group or an aryl group; B is a substituted or unsubstituted C1-C20 alkyl, cycloalkyl, alkaryl, alkaryl or aryl group or an alkylamino group and at least one of $X^1$, $X^2$, $Y^1$, $Y^2$ or Z is a C1-C10 alkyl, cycloalkyl, alkaryl, aralkyl or alkoxy substituting group.

The invention further provides a method for preparing a diamine of formula (I) comprising the steps of forming a substituted spiroimidazole from a substituted diketone of formula (II), where $X^1$, $X^2$, $Y^1$, $Y^2$ and Z are as above, reducing the substituted spiroimidazole to form a substituted diamine, optionally resolving the substituted diamine to an enantiomerically enriched form, and sulphonylating the substituted diamine.

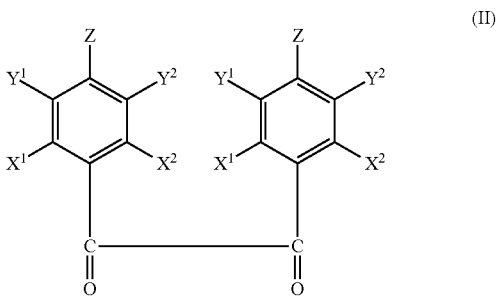

(II)

The invention also provides a catalyst comprising the reaction product of a diamine of formula (I) and a suitable compound of a catalytically active metal.

DETAILED DESCRIPTION

In formula (I), A is hydrogen or a saturated or unsaturated C1-C20 alkyl group or an aryl group. The C1-C20 alkyl groups may be branched or linear, for example may be methyl, ethyl, n-propyl, iso-propyl, n-butyl, iso-butyl, sec-butyl, tert-butyl, pentyl, hexyl, cyclohexyl, ethyl-hexyl, iso-octyl, n-nonyl, n-decyl, iso-decyl, tridecyl, octadecyl and isooctadecyl. The aryl group may be an unsubstituted or substituted phenyl, naphthyl or anthracylphenyl. Suitable substituting groups are hydroxy, halide (e.g. F, Cl, Br, I), C1-C20 alkoxy, amino, amido, nitrile and thiol. Preferably A is hydrogen, methyl ethyl, propyl or phenyl. Most preferably A is hydrogen.

In formula (I), B is introduced by sulphonylation of the optionally enantiomerically enriched substituted diamine. A wide range of sulphonylation compounds may be used to alter the properties of the sulphonylated diamine of formula (I). Accordingly, B may be a substituted or unsubstituted C1-C20 alkyl, cycloalkyl, alkaryl, alkaryl or aryl group, for example as described above, or an alkylamino group. By "alkylamino" we mean that B may be of formula —$NR'_2$, where R' is e.g. methyl, cyclohexyl or isopropyl or the nitrogen forms part of an alkyl ring structure. Fluoroalkyl or fluoroaryl groups may be used, for example B may be p-$CF_3$—$C_6H_4$, $C_6F_5$ or $CF_2CF_2CF_2CF_3$ or $CF_3$. Preferably B is an aryl group. The aryl group may be an unsubstituted or substituted phenyl, naphthyl or anthracylphenyl or heteroaryl compound such as pyridyl. Suitable substituting groups are C1-C20 alkyl as described above, trifluoromethyl, hydroxyl, halide (e.g. F, Cl, Br, I), C1-C20 alkoxy (especially methoxy), amino, amido, nitrile, nitro and thiol. Hence B may be for example o-Nitrophenyl, p-nitrophenyl, trichlorophenyl, trimethoxyphenyl, triisopropylphenyl, o-aminophenyl, benzyl (—$CH_2C_6H_5$), 2-phenylethyl ($C_2H_4C_6H_5$), phenyl ($C_6H_5$), tolyl (p-$CH_3$—$C_6H_4$), xylyl (($CH_3)_2C_6H_3$), anisyl ($CH_3O$—$C_6H_4$), naphthyl or dansyl (5-dimethylamino-1-naphthyl). Preferably, B is tolyl and the sulphonylation is performed with tosyl chloride (p-toluenesulphonyl chloride).

The diamine of the present invention has two chiral centres, each bearing a phenyl ring having at least one substituting group $X^1, X^2, Y^1, Y^2$ or Z. The substituting group $X^1, X^2, Y^1, Y^2$ or Z is a C1-C10 alkyl, cycloalkyl, alkaryl, aralkyl or alkoxy group. It will be understood that in order to satisfy the valency of the carbon atoms in the phenyl rings to which $X^1, X^2, Y^1, Y^2$ or Z is bound, where $X^1, X^2, Y^1, Y^2$ or Z is not a C1-C10 alkyl, cycloalkyl, alkaryl, aralkyl or alkoxy substituting group, $X^1, X^2, Y^1, Y^2$ or Z will be a hydrogen atom.

Thus at least one of $X^1, X^2, Y^1, Y^2$ or Z may independently be a C1-C10 alkyl group such as methyl, trifluoromethyl, ethyl, n-propyl, iso-propyl, n-butyl, iso-butyl, sec-butyl, tert-butyl, pentyl, cyclopentyl, hexyl, cyclohexyl, ethyl-hexyl, iso-octyl, n-nonyl, n-decyl or iso-decyl; an alkaryl group such as benzyl or ethylphenyl; an aryl group such as phenyl, tolyl or xylyl; or a C1-C10 alkoxy group such as methoxy, ethoxy, n-propoxy, iso-propoxy, n-butoxy, iso-butoxy, sec-butoxy, tert-butoxy, cyclopentoxy, pentoxy, hexoxy, cyclohexoxy, ethyl-hexoxy, iso-octoxy, n-nonoxy, n-decoxy or iso-decoxy.

Preferably each phenyl ring has one or more substituents. The phenyl rings may be substituted in one or more positions, i.e. the rings may be mono-, di-, tri-, tetra- or penta-substituted. The substituting group on the phenyl ring may be in the ortho ($X^1, X^2$), meta ($Y^1, Y^2$) or para (Z) position. However, when the substituent is at the mete-position of the phenyl ring it minimizes the electronic effects on the amino group, which may facilitate the synthesis of the resulting diamine. Thus one embodiment the substituted diamine is a 1,2-di-(meta-substituted phenyl)ethylenediamine. Where more that one substituting group is present they are preferably the same. For example in one embodiment, $Y^1, Y^2$ may be hydrogen and $X^1, X^2$ and Z are preferably the same alkyl, cycloalkyl, alkaryl, aralkyl or alkoxy substituting group. In an alternative embodiment $X^1, X^2$ and Z may be hydrogen and $Y^1$ and $Y^2$ are preferably the same alkyl, cycloalkyl, alkaryl, aralkyl or alkoxy substituting group. In a preferred embodiment $X^1, X^2, Y^1$ and $Y^2$ are hydrogen and Z is a C1-C10 alkyl, cycloalkyl, alkaryl, aralkyl or alkoxy substituting group. In a particularly preferred embodiment, $X^1, X^2, Y^1$ and $Y^2$ are hydrogen and Z is methyl. In another particularly preferred embodiment, $X^1, X^2, Y^1$ and $Y^2$ are hydrogen and Z is methoxy.

The substituted diamines of the present invention may be conveniently made from substituted diketones of formula (II) where $X^1, X^2, Y^1, Y^2$ and Z are as above, via a spiro-imidazole, which is then reduced to a diamine and sulphonylated.

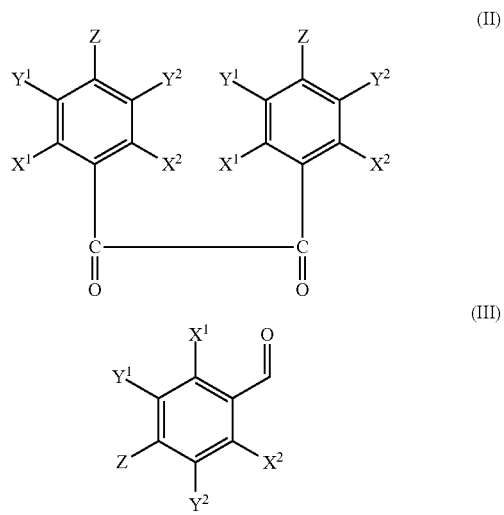

Substituted diketones (benzils) of formula (II) can be obtained commercially or can be readily prepared from substituted benzaldehydes of formula (III) where $X^1, X^2, Y^1, Y^2$ and Z are as above, by benzoin condensation followed by oxidation of the resulting substituted benzoin. Substituted benzaldehydes are commercially available or may be synthesised using known substitution reactions. Benzoin condensation reactions are well known and are typically performed by reacting a substituted benzaldehyde in a suitable solvent in the presence of sodium cyanide (see for example Ide et al, *Org. React.* 1948, 4, 269-304). The oxidation of the substituted benzoin to the diketone may readily be performed using copper acetate and ammonium nitrate (for example see Weiss et al, *J. Am. Chem. Soc,* 1948, 3666).

The spiroimidazole may be formed by treating the substituted diketone of formula (II) with acetic acid, ammonium acetate and cyclohexanone and heating to reflux. The reduction of the resulting substituted benzoin to the substituted diamine may be performed by mixing a solution of the spiroimidazole with lithium wire and liquid ammonia at below −60° C., treating the mixture with ethanol and ammonium chloride and allowing the mixture to warm to room temperature. The substituted diamine is sulphonylated to provide the substituted diamines of the present invention.

The substituted diamine may then be sulphonylated by treating the substituted diamine in a suitable solvent with the desired sulphonyl chloride, i.e. Cl—SO$_2$—B, and a base such as triethylamine.

The nitrogen atoms in the substituted diamine are bonded to chiral centres and so the substituted diamine is chiral. The diamine may be homochiral, i.e. (R,R) or (S,S), or have one (R) and one (S) centre. Preferably the diamine is homochiral. Whereas the diamine may be used as a racemic mixture, the amine is preferably enantiomerically enriched. The resolution of the chiral substituted diamine may be performed using a chiral acid or by any other method known to those skilled in the art. Whereas the resolution may be performed on the sulphonylated diamine of formula (I), preferably the resolution is performed on the substituted diamine before the sulphonylation step. For example, the substituted diamine may be treated with a chiral carboxylic acid such as ditoluoyltartaric acid or dibenzoyltartaric acid in a suitable solvent. The resolved substituted diamine preferably has an enantiomeric excess (ee %)>70%, more preferably >90%.

Hence this route provides an efficient and cost effective method to prepare enantiomerically enriched substituted 1,2-diphenylethylenediamines. The route is depicted below for a preferred example where A, $X^1$, $X^2$, $Y^1$ and $Y^2$ are hydrogen, B is e.g. p-CH$_3$—C$_6$H$_5$ and Z is a C1-C10 alkyl, cycloalkyl, alkaryl, aralkyl or alkoxy substituting group;

ticularly Ru or Rh. Suitable Ru or Rh compounds are [MX$_2$(arene)]$_2$ compounds where M=Rh or Ru and X=halogen, more preferably [RuCl$_2$(arene)]$_2$. Arene compounds are any suitable aromatic molecule, and include benzenes and cyclopentadienes, e.g. benzene, pentamethylcyclopentadiene and para-cymene (4-isopropyltoluene). Particularly suitable metal compounds for preparing hydrogenation catalysts include [RhCp*Cl$_2$]$_2$ (where Cp* is CpMe$_5$), [RuCl$_2$(benzene)]$_2$ and [RuCl$_2$(p-cymene)]$_2$.

The catalysts may be prepared by simply combining the diamine and the metal compound in a suitable solvent under mild conditions (e.g. 0 to 80° C. at about atmospheric pressure). Suitable solvents include hydrocarbons, aromatic hydrocarbons, chlorinated hydrocarbons, esters, alcohols, ethers, DMF and the like. If desired, the reaction may be performed ex-situ and the resulting catalyst isolated, e.g. by removal of the solvent under vacuum. Alternatively, the catalyst may be formed in-situ, i.e. in the presence of the substrate to be hydrogenated and the hydrogen source, again by combining the metal compound and diamine in the reactants, which may be diluted with a suitable solvent.

The chiral catalysts of the present invention may be applied to transfer hydrogenation reactions. Typically, a carbonyl compound or imine, hydrogen source, base and solvent are mixed in the presence of the catalyst, which may be formed in-situ. Preferred hydrogen sources are isopropanol or formic acid (or formates). The catalysts may be used to reduce a wide

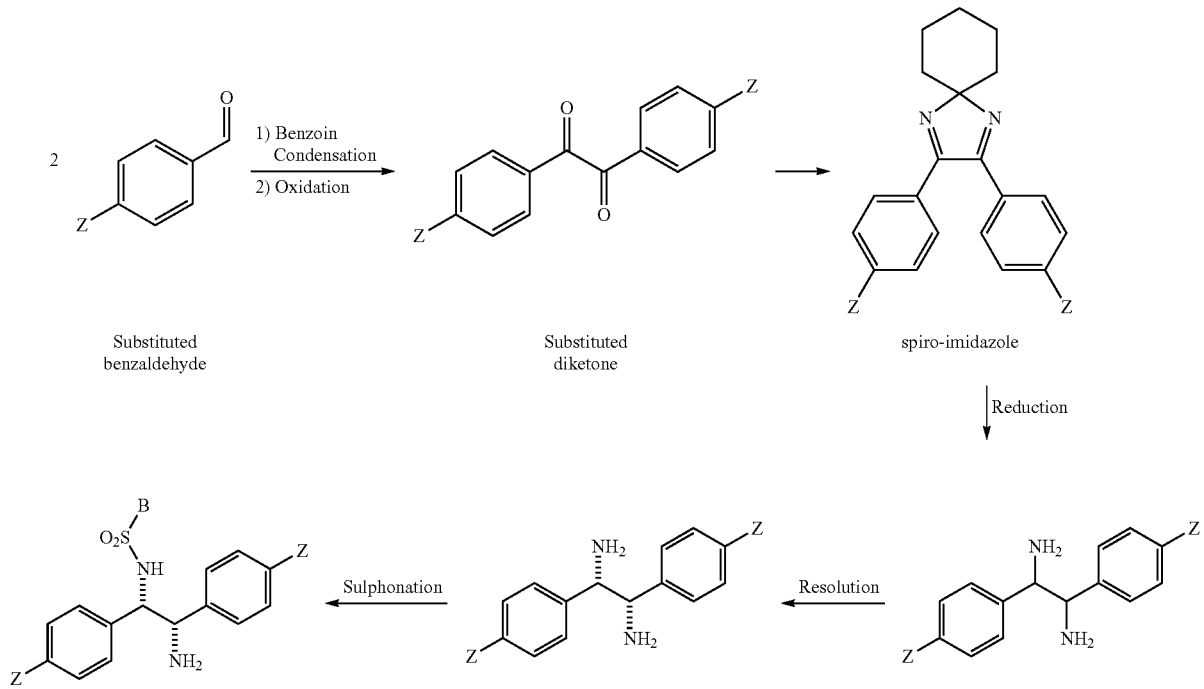

Catalysts suitable for performing asymmetric transfer hydrogenation reactions may be prepared by reacting the substituted sulphonylated diamines of the present invention with a suitable compound of a catalytically active metal. The metal compound is preferably a compound of metals selected from the list consisting of Ru, Rh, Ir, Co, Ni, Fe, Pd or Pt. Preferred compounds are compounds of Ru, Rh and Ir, parvariety of carbonyl compounds to the corresponding chiral alcohols and imines to the corresponding chiral amines. The reactions may be carried out under typical transfer hydrogenation conditions and in a variety of suitable solvents known to those skilled in the art. For example, the reaction may be performed in an ether, ester or dimethylformamide (DMF) at 0-75° C. Water may be present. With formic acid, a base such as triethylamine, DBU or other tertiary amine is preferably used. With isopropanol, the base is preferably t-BuOK, KOH or iPrOK.

The invention is illustrated by the following examples.

Example 1

Preparation of Diamine Ligands (I) Spiro-Imidazole Formation (1 to 2)

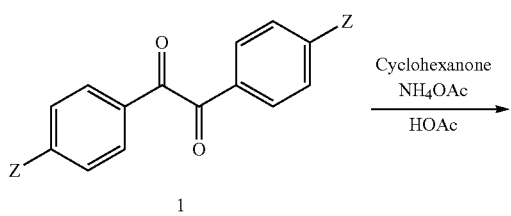

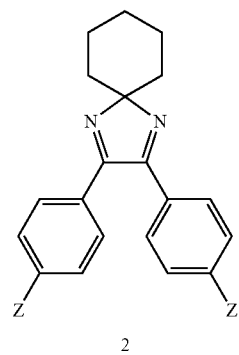

a) Z=Methyl (CH$_3$): Acetic acid (70 ml) was added to a flask containing the commercially available diketone 1a (dimethylbenzil 11.9 g, 50 mmol) and ammonium acetate (27 g, 350 mmol). Cyclohexanone (5.3 ml, 51.5 mmol) was added and the reaction mixture was heated at reflux for 1-4 hours. After cooling to room temperature, the mixture was poured onto water and left overnight to crystallize. The crystals were collected by filtration and dried under reduced pressure. Recrystallization was from ethyl acetate/hexane and gave 8.22 and 3.32 g of 2a in 2 crops. Total yield 11.54 g, 73%.

b) Z=Methoxy (CH$_3$O): Acetic acid (100 ml) was added to a flask containing the commercially available diketone 1b (dimethoxybenzil, 18.9 g, 70 mmol) and ammonium acetate (37.7 g, 490 mmol). Cyclohexanone (7.45 ml, 72.1 mmol) was added and the reaction mixture was heated at reflux for 1-4 hours. After cooling to room temperature, the mixture was poured onto water and left overnight to crystallize. The crystals were collected by filtration and dried under reduced pressure. Yield of imidazole 2b, 19.22 g, 79%. Further purification can be achieved by crystallisation from ethyl acetate/hexane.

(II) Reduction (2 to 3)

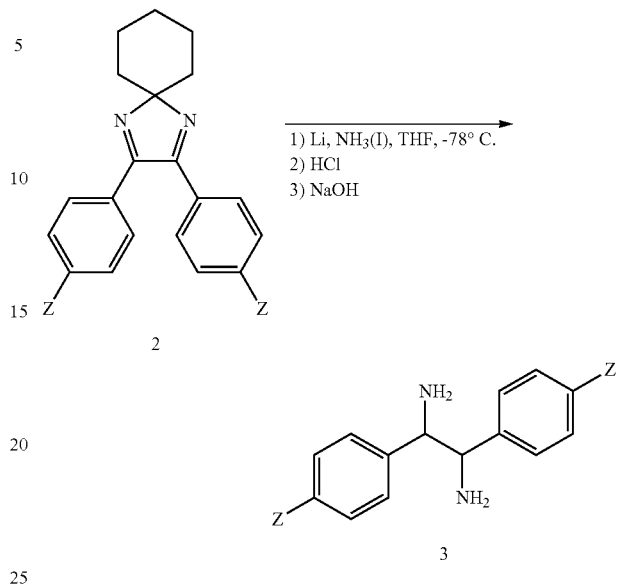

a) Z=Methyl (CH$_3$): Ammonia gas was slowly condensed into a solution of the spiro-imidazole 2a (6.95 g, 22 mmol) in anhydrous THF (50 ml) at −78° C. under argon. Once the volume of the reaction mixture has approximately doubled, the gas flow was stopped. Lithium wire (0.62 g, 88 mmol) was added slowly ensuring that the temperature did not exceed −60° C. After stirring for 30-60 minutes ethanol (2.6 ml) was added, and 30-60 minutes later ammonium chloride (6.2 g) was added. The mixture was allowed to warm to room temperature and water (about 100 ml) and MTBE (about 100 ml) were added. The layers were separated and the aqueous layer was extracted twice with about 100 ml MTBE. The combined organic layers were washed with brine and evaporated under vacuum. The resulting oil was dissolved in MTBE and 10% HCl was added (2-3 eq.). The biphasic mixture was stirred for 30-90 minutes and was diluted with water. The layers were separated and the organic layer was extracted with water. The combined aqueous layers were washed with dichloromethane and then neutralised with aqueous KOH until the pH>10. The crude diamine was extracted into dichloromethane (3 times). The combined organic extracts dried (Na$_2$SO$_4$) and evaporated to give an oil or solid. Yield of racemic diamine 3a as a 19:1 mixture of diastereoisomers, 4.96 g, 94%. Further purification can be achieved by crystallisation from ethyl acetate/hexane.

b) Z=Methoxy (CH$_3$O): Ammonia gas was slowly condensed into a solution of the spiro-imidazole 2b (6.96 g, 20 mmol) in anhydrous TI-IF (40 ml) at −78° C. under argon. Once the volume of the reaction mixture has approximately doubled, the gas flow was stopped. Lithium wire (0.56 g, 80 mmol) was added slowly ensuring that the temperature did not exceed −60° C. After stirring for 30-60 minutes ethanol (2.4 ml) was added, and 30-60 minutes later ammonium chloride (2.8 g) was added. The mixture was allowed to warm to room temperature and water (about 100 ml) and MTBE (about 100 ml) were added. The layers were separated and the aqueous layer was extracted twice with about 100 ml MTBE. The combined organic layers were washed with brine and evaporated under vacuum. The resulting oil was dissolved in MTBE and 10% HCl was added (2-3 eq.). The biphasic mixture was stirred for 30-90 minutes and was diluted with water. The layers were separated and the organic layer was extracted with water. The combined aqueous layers were washed with dichloromethane and then neutralised with aqueous KOH until the pH>10. The crude diamine was extracted into dichloromethane (3 times). The combined organic extracts dried ($Na_2SO_4$) and evaporated to give an oil or solid. Yield of racemic diamine 3b as a 19:1 mixture of diastereoisomers, 4.69 g, 86%. Further purification can be achieved by crystallisation from ethyl acetate/hexane.

(III) Chiral Resolution of Diamines

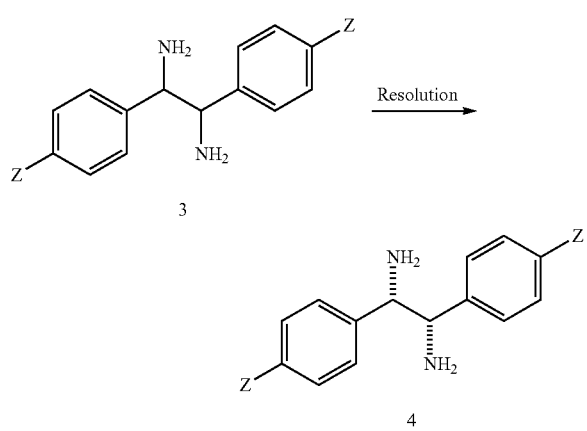

a) Resolution of diamine 3a. Formation of a salt with ditoluoyltartaric acid in methanol and crystallisation from methanol initially gave (R,R) 4a in 94% ee. This can be increased to >99% with one further crystallisation.

b) Resolution of diamine 3b. Formation of a salt with ditoluoyltartaric acid in methanol and crystallisation from methanol initially gave (S,S) 4b in 74% ee. It should be possible to increase the ee by further crystallisation. Formation of a salt with dibenzoyltartaric acid in methanol and crystallisation from methanol initially gave 4b in 98% ee.

(IV) Synthesis of Mono-Sulfonylated Diamines

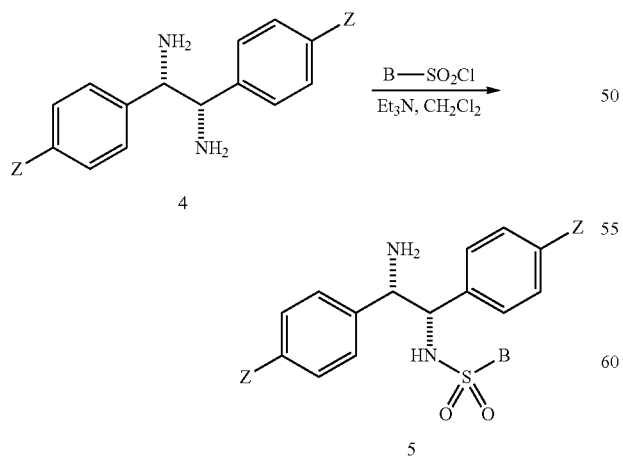

a) Tosyl-5a ($Z=CH_3$, $B=4-CH_3-C_6H_4$). Triethylamine (210 μl, 1.5 mmol) was added to a solution of the diamine 4a (180 mg, 0.75 mmol) in anhydrous dichloromethane (8 ml) and the solution was cooled to 0° C. A solution of the tosyl chloride (p-toluenesulphonyl chloride, 148 mg, 0.77 mmol) in anhydrous dichloromethane (4 ml) was added slowly. The mixture was stirred at 0° C. for 30-120 minutes and allowed to warm to room temperature over 1-24 hours. Water was added and the layers separated. The aqueous layer was extracted twice with dichloromethane and the combined organic layers were washed with brine, dried ($Na_2SO_4$) and evaporated. The crude mono-sulfonated diamine could be purified by column chromatography. Purification by column chromatography gave 270 mg (91%) of Ts-5a as a white solid.

b) Tosyl-5b ($Z=OCH_3$, $B=4-CH_3-C_6H_4$). Triethylamine (190 μl, 1.3 mmol) was added to a solution of the diamine 4b (175 mg, 0.65 mmol) in anhydrous dichloromethane (8 ml) and the solution was cooled to 0° C. A solution of the tosyl chloride (p-toluenesulphonyl chloride, 1428 mg, 0.67 mmol) in anhydrous dichloromethane (5 ml) was added slowly. The mixture was stirred at 0° C. for 30-120 minutes and allowed to warm to room temperature over 1-24 hours. Water was added and the layers separated. The aqueous layer was extracted twice with dichloromethane and the combined organic layers were washed with brine, dried ($Na_2SO_4$) and evaporated. The crude mono-sulfonylated diamine could be purified by column chromatography. Purification by column chromatography gave 270 mg (91%) of Ts-5b as a white solid.

Example 2

Preparation of Transfer Hydrogenation Catalyst

A mixture of $[Ru(p-cymene)Cl_2]_2$ (0.5 eq.), triethylamine (2 eq.), mono-sulfonated diamine (1 eq.) 5b in anhydrous isopropanol was heated at 70-90° C. for 1-4 hours under an inert atmosphere. After cooling to room temperature the solution was concentrated under reduced pressure and the orange solid collected by filtration. The solid was washed with degassed water and a small amount of methanol then further dried under reduced pressure. Further purification can be performed by precipitation/crystallisation from hot methanol.

Example 3

Use of Mono-Sulfonated Diamines 5 for Asymmetric Transfer Hydrogenation Test of Transfer Hydrogenation Catalysts on a Mixture of Ketones Transfer hydrogenation catalysts bearing diamines 5 were prepared in situ and tested on pre-formed mixture of ketones in DMF. $[Ru(p-cymene)Cl_2]_2$ (0.0025 mmol) or $[RhCp*Cl_2]_2$ (0.0025 mmol) mono-sulfonated diamine (0.0055 mmol) 5 in anhydrous DMF (2 mL) were heated at 40° C. for 10 minutes under inert atmosphere (argon). A solution of five ketones (0.5 mL, 1 mmol in total, 0.2 mmol each) in DMF was added (S/C 40 with respect to each substrate), followed by 0.6 mL of formic acid/trietylamine 1/1 mixture and 1 mL of DMF. The reaction was heated overnight (20 hrs) at 60° C. and analysed by CG (ChiraDex CB column, 10 psi He, 100° C. for 12 min, then to 180° C. at 1.5° C./min, then to 200° C. at 5° C./min).

For reference, the diamines tested were as follows:

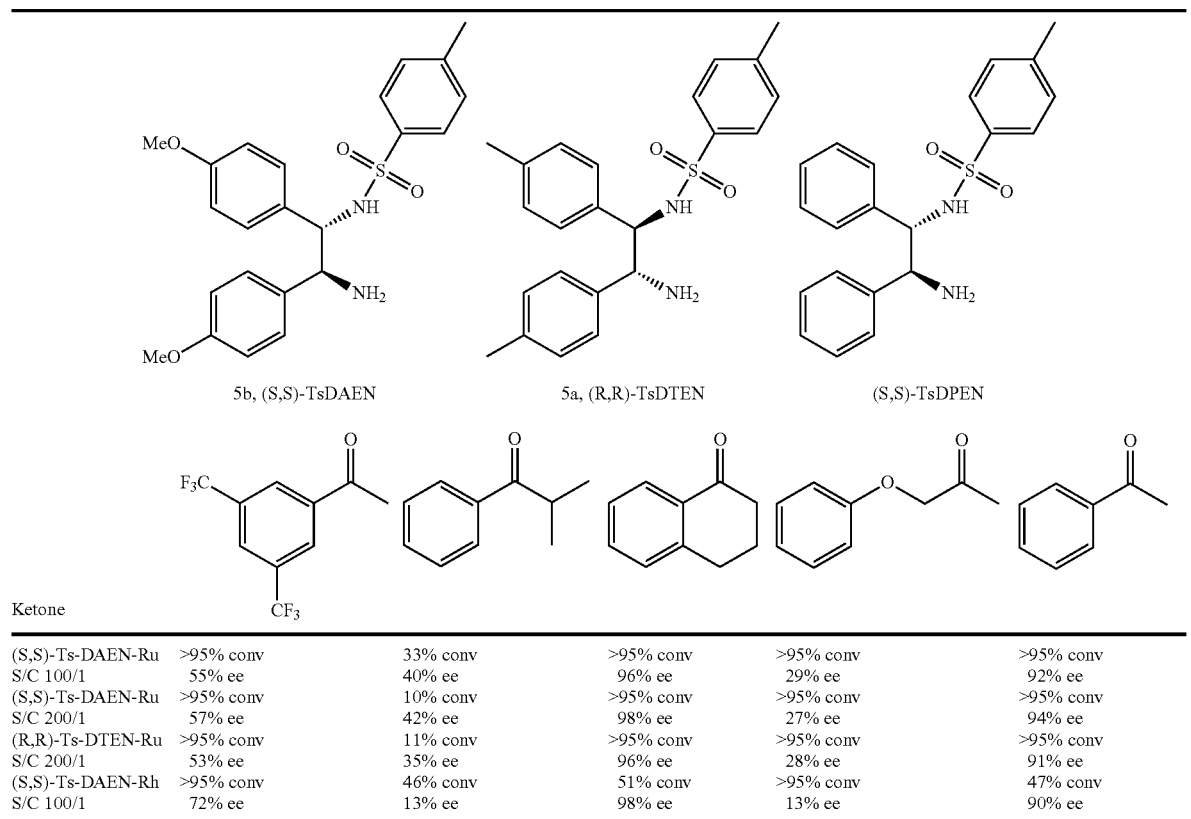

| | | | | | |
|---|---|---|---|---|---|
| (S,S)-Ts-DAEN-Ru S/C 100/1 | >95% conv 55% ee | 33% conv 40% ee | >95% conv 96% ee | >95% conv 29% ee | >95% conv 92% ee |
| (S,S)-Ts-DAEN-Ru S/C 200/1 | >95% conv 57% ee | 10% conv 42% ee | >95% conv 98% ee | >95% conv 27% ee | >95% conv 94% ee |
| (R,R)-Ts-DTEN-Ru S/C 200/1 | >95% conv 53% ee | 11% conv 35% ee | >95% conv 96% ee | >95% conv 28% ee | >95% conv 91% ee |
| (S,S)-Ts-DAEN-Rh S/C 100/1 | >95% conv 72% ee | 46% conv 13% ee | 51% conv 98% ee | >95% conv 13% ee | 47% conv 90% ee | conv = conversion
ee enantiomeric excess

The results show particularly high conversions and ee's are obtained for the cyclic ketone, i.e. where the ketone is part of a ring structure, such as α-tetralone.

Example 4

Activity of TsDAEN vs. TsDPEN

The activity of (S,S)-TsDAEN vs the conventional (S,S)-TsDPEN in asymmetric transfer hydrogenation was tested using α-tetralone as a substrate. The reaction was performed on a 15 mmol scale, at S/C 500/1, using [RuCl$_2$(p-cymene)]$_2$ as metal precursor and DMF as solvent at 60° C. One equivalent of triethylammonium formate was added at the beginning of the reaction and more HCOOH was added during the course of the reaction to maintain the pH at 8.2. The results shown below indicate that (S,S)-TsDAEN is more active than (S,S)-TsDPEN.

| | Diamine Ligand | Time (h) | Conversion (%) | e.e. (%) |
|---|---|---|---|---|
| Example 4 | (S,S)-TsDAEN | 1.5 | 36 | 98 |
| | | 5 | 71 | |
| | | 22 | 90 | |

-continued

| | Diamine Ligand | Time (h) | Conversion (%) | e.e. (%) |
|---|---|---|---|---|
| Comparative Example | (S,S)-TsDPEN | 1 | 11 | 98 |
| | | 2 | 25 | |
| | | 3 | 31 | |
| | | 4 | 36 | |
| | | 6 | 45 | |
| | | 22 | 70 | |

What is claimed is:
1. A diamine of formula (I)

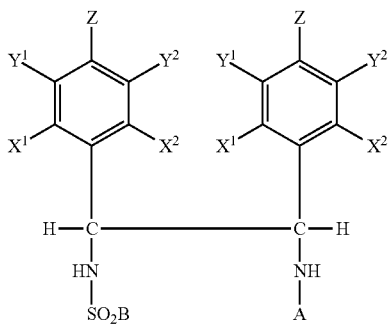

in which A is hydrogen or a saturated or unsaturated C1-C20 alkyl group or an aryl group; B is a substituted or unsubstituted C1-C20 alkyl, cycloalkyl, alkaryl, or aryl group or an alkylamino group and either (i) Z is hydrogen and at least one of $X^1$, $X^2$, $Y^1$ and $Y^2$ is a C1-C10 alkyl, cycloalkyl, alkaryl, aralkyl or alkoxy substituting group or (ii) Z is a C1-C10 alkyl, alkaryl, cycloalkyl, aralkyl or alkoxy substituting group and at least one of $X^1$, $X^2$, $Y^1$, $Y^2$ and Z is a C1-C10 alkyl, alkaryl, cycloalkyl, aralkyl or alkoxy substituting group.

2. The diamine according to claim 1 wherein A is hydrogen.

3. The diamine according to claim 1 wherein B is a substituted or unsubstituted aryl group.

4. The diamine according to claim 1 wherein Z is hydrogen and at least one of $X^1$, $X^2$, $Y^1$ and $Y^2$ is a C1-C10 alkyl, alkaryl, cycloalkyl, aralkyl or alkoxy substituting group.

5. The diamine according to claim 1 wherein Z is a C1-C10 alkyl, alkaryl, cycloalkyl, aralkyl or alkoxy substituting group and at least one of $X^1$, $X^2$, $Y^1$, $Y^2$ and Z are a C1-C10 alkyl, alkaryl, cycloalkyl, aralkyl or alkoxy substituting group.

6. The diamine according to claim 5 wherein one of $X^1$, $X^2$, $Y^1$ and $Y^2$ is a C1-C10 alkyl, alkaryl, cycloalkyl, aralkyl or alkoxy substituting group.

7. The diamine according to claim 1 wherein the diamine is homochiral.

8. The method for preparing a diamine of formula (I) as claimed in claim 1 comprising the steps of
    a) forming a substituted spiroimidazole from a substituted diketone of formula (II),
    b) reducing the substituted spiroimidazole to form a substituted diamine,
    c) optionally resolving the substituted diamine to an enantiomerically enriched form, and
    d) sulphonylating the substituted diamine

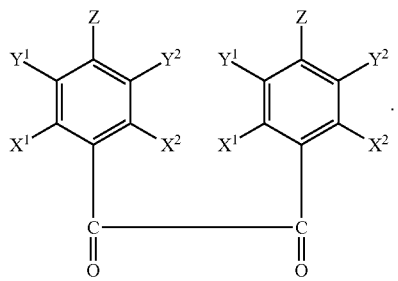

9. A catalyst comprising the reaction product of a diamine of formula (I) as claimed in claim 1 and a compound of a metal selected from the list consisting of Ru, Rh, Ir, Co, Ni, Fe, Pd or Pt.

10. The catalyst according to claim 9 wherein the metal compound is $[MX_2(arene)]_2$ where M=Rh or Ru and X=halogen.

11. A method comprising contacting the catalyst according to claim 9 with a compound and performing a transfer hydrogenation reaction.

12. The method according to claim 11 wherein the compound is a cyclic ketone.

13. The diamine according to claim 5 wherein two of $X^1$, $X^2$, $Y^1$ and $Y^2$ are a C1-C10 alkyl, alkaryl, cycloalkyl, aralkyl or alkoxy substituting group.

14. The diamine according to claim 5 wherein three of $X^1$, $X^2$, $Y^1$ and $Y^2$ are a C1-C10 alkyl, alkaryl, cycloalkyl, aralkyl or alkoxy substituting group.

15. The diamine according to claim 5 wherein four of $X^1$, $X^2$, $Y^1$ and $Y^2$ are a C1-C10 alkyl, alkaryl, cycloalkyl, aralkyl or alkoxy substituting group.

16. The diamine according to claim 3 wherein B is a substituted phenyl group.

17. The diamine according to claim 4 wherein B is 4-methylphenyl, 4-methoxyphenyl or 4-chlorophenyl.

18. The diamine according to claim 5 wherein B is 4-methylphenyl.

19. The diamine according to claim 4 wherein B is 1-naphthyl.

20. The diamine according to claim 1 wherein B is benzyl.

21. The diamine according to claim 1 wherein B is methyl.

22. The catalyst according to claim 10 wherein the metal compound is $[MCl_2(p\text{-cymene})]_z$.

23. A method of reducing a compound comprising contacting the catalyst according to claim 9 with an unreduced form of a 10-hydroxy-dihydro-dibenz-[b,f]-azepine under conditions suitable for performing a transfer hydrogenation reaction.

* * * * *

UNITED STATES PATENT AND TRADEMARK OFFICE
CERTIFICATE OF CORRECTION

PATENT NO.         : 8,859,815 B2                                    Page 1 of 1
APPLICATION NO.    : 13/313889
DATED              : October 14, 2014
INVENTOR(S)        : Beatriz Dominguez et al.

It is certified that error appears in the above-identified patent and that said Letters Patent is hereby corrected as shown below:

In the Claims

In Column 14, claim 22, line 41, replace "[MCl$_2$(p-cymene)]$_z$" with -- [MCl$_2$(p-cymene)]$_2$ --.

Signed and Sealed this
Thirteenth Day of January, 2015

Michelle K. Lee
*Deputy Director of the United States Patent and Trademark Office*